US007090856B2

(12) United States Patent
Qian et al.

(10) Patent No.: US 7,090,856 B2
(45) Date of Patent: Aug. 15, 2006

(54) **ANTI-FOULING EXOPOLYSACCHARIDES ISOLATED FROM CULTURES OF *VIBRIO ALGINOLYTICUS* AND *VIBRIO PROTEOLYTICUS***

(75) Inventors: Pei-Yuan Qian, Clear Water Bay (HK);
Serguei Dobretsov, Sai Kung (HK);
Tilmann Harder, Oldenburg (DE);
Chun Kwan Stanley Lau, Sai Kung (HK)

(73) Assignee: Hong Kong University of Science and Technology (HK)

( * ) Notice: Subject to any disclaimer, the term of this patent is extended or adjusted under 35 U.S.C. 154(b) by 5 days.

(21) Appl. No.: 10/465,448

(22) Filed: Jun. 19, 2003

(65) Prior Publication Data

US 2004/0258655 A1 Dec. 23, 2004

(51) Int. Cl.
*A61K 39/106* (2006.01)
*A61K 39/02* (2006.01)
*A61K 35/00* (2006.01)
*A61K 31/74* (2006.01)
*A61K 37/715* (2006.01)
*C09D 5/14* (2006.01)

(52) U.S. Cl. .................. 424/261.1; 424/116; 424/123; 424/234.1; 424/78.09; 514/54; 106/15.05

(58) Field of Classification Search ............... 424/93.1, 424/93.3, 93.47, 115, 123, 114, 261.1, 78.09; 106/15.05
See application file for complete search history.

(56) References Cited

U.S. PATENT DOCUMENTS

| | | | |
|---|---|---|---|
| 3,854,960 A * | 12/1974 | Plum et al. ............... | 106/18.31 |
| 4,234,340 A | 11/1980 | Pellico | |
| 4,788,302 A * | 11/1988 | Costlow et al. ............ | 549/299 |
| 4,908,061 A | 3/1990 | Nanishi et al. | |
| 5,218,059 A | 6/1993 | Kishihara et al. | |
| 5,607,741 A | 3/1997 | Zimmerman et al. | |
| 5,695,552 A | 12/1997 | Taylor | |
| 5,919,689 A | 7/1999 | Selvig et al. | |
| 5,958,116 A | 9/1999 | Kishihara et al. | |
| 5,989,323 A | 11/1999 | Taylor | |
| 5,998,200 A | 12/1999 | Bonaventura et al. | |
| 6,057,288 A | 5/2000 | Pearson et al. | |
| 6,136,579 A | 10/2000 | Jackson | |
| 6,194,178 B1 | 2/2001 | Palcic et al. | |
| 6,337,347 B1 | 1/2002 | Livinghouse | |
| 6,436,680 B1 * | 8/2002 | Guezennec et al. ......... | 435/101 |
| 6,455,031 B1 | 9/2002 | Davies et al. | |

FOREIGN PATENT DOCUMENTS

| | | |
|---|---|---|
| CN | 1341602 A | 3/2002 |
| CN | 1341664 A | 3/2002 |
| CN | 1341665 A | 3/2002 |
| JP | 63-174933 A | 7/1988 |
| JP | 03-239766 | 10/1991 |
| JP | 03-239766 A | 10/1991 |
| JP | 04-271791 A | 9/1992 |
| JP | 05-252970 A | 10/1993 |
| JP | 08-256763 A | 10/1996 |
| JP | 2000-245497 | 9/2000 |
| WO | WO 00/47204 A1 | 8/2000 |

OTHER PUBLICATIONS

Tubiash et al., 1965. Bacillary necrosis, a disease of larval and juvenile bivalve mollusks. J. Bacteriology 90: 1036-1044.*
Wai et al., 2002. *Vibrio cholerae* O1 strain TSI-4 produces the exopolysaccharide materials that determine colony morphology, stress resistance and biofilm formation. Applied and Environmental Microbiology 64: 3648-3655.*
Rodrigues et al., 1991. Exopolysaccharide production by *Vibrio fischeri*, a fouling marine bacterium. Biofouling 4:301-308.*
Muralidharan et al., 2003. Physicochemical analyses of the exopolysaccharides produced by a marine biofouling bacterium, *Vibrio alginolyticus*. Process Biochemistry 38:841-847.*
ATCC entries for bacteria 19108 and 19105. Site accessed Mar. 30, 2005.*
Dictionary.com entry for "necrosis". Site accessed Mar. 31, 2005.*
Dictionary.com definition of "antifouling", accessed Jul. 11, 2005. 1 page.*
Bryan et al., "*Induction of larval settlement and metamorphosis by pharmacological and conspecific associated compounds in the serpulid polychaete Hydroides elegans*", Mar Ecol Prog. Ser 146: 81-90, (1997).
Claisse & Alzieu, "*Copper Contamination as a Result of Antifouling Paint Regulations*", Marine Pollution Bulletin vol. 26/No. 7/ Jul. 1993, pp. 395-397.
Clare et al., "*Molecular approaches to nontoxic antifouling*", Invertebrate Reproduction and Development, 22:1-3 (1992), pp. 67-76.
Fisher et al., "*Decreased resistance of eastern oysters (Crassostrea virginica) to a protozoan pathogen (Perkinsus marinus) after sublethal exposure to tributyltin oxide*", Marine Environmental Research 47 (1999), pp. 185-201.
Hashimoto et al., "*Concentration and Distribution of Butyltin Compounds in a Heavy Tanker Route in the Strait of Malacca and in Tokyo Bay*", Marine Environmental Research, vol. 45, No. 2, (1998), pp. 169-177.

(Continued)

*Primary Examiner*—Irene Marx
*Assistant Examiner*—Lora E Barnhart
(74) *Attorney, Agent, or Firm*—Brinks Hofer Gilson & Lione; G. Peter Nichols

(57) ABSTRACT

An anti-fouling agent derived by culturing *Vibrio alginolyticus* in a suitable aqueous solution as well as a newly isolated strain of *V. alginolyticus* (DSM 15590) for producing the anti-fouling agent. The anti-fouling agent can be used as a component to produce other anti-fouling compositions, Depending on the use, the anti-fouling agent derived from *V. alginolyricus* may be use directly, or subject to further purification.

14 Claims, 3 Drawing Sheets

OTHER PUBLICATIONS

Maki et al., "*Inhibition of attachment of larval barnacles, Balanus amphitrite, by bacterial surface films*", Marine Biology 97, (1988), pp. 199-206.

Matthiessen, P., et al., "*Critical Appraisal of the Evidence for Tributyltin-Mediated Endocrine Disruption in Mollusks*", Environmental Toxicology and Chemistry, vol. 17, No. 1, (1998), pp. 37-43.

Rittschof D., "*Fouling and Natural Products as Antifoulants*", Recent Advances in Marine Biotechnology, vol. 3. Science Publishers, Inc., NH, (1997), pp. 245-257.

Wieczorek et al., "*Inhibitory and facilitatory effects of microbial films on settlement of Balanus amphitrite amphitrite larvae*", Mar. Ecol. Prog. Ser. 119: (1995), pp. 221-226.

* cited by examiner

5'AAGTCGAGCGGAAACGAGTTATCTGAACCTTCGGGGAACGATAACG
GCGTCGAGCGGCGGACGGGTGAGTAATGCCTAGGAAATTGCCCTGAT
GTGGGGGATAACCATTGGAAACGATGGCTAATACCGCATGATGCCTAC
GGGCCAAAGAGGGGGACCTTCGGGCCTCTCGCGTCAGGATATGCCTA
GGTGGGATTAGCTAGTTGGTGAGGTAAGGGCTCACCAAGGCGACGAT
CCCTAGCTGGTCTGAGAGGATGATCAGCCACACTGGAACTGAGACAC
GGTCCAGACTCCTACGGGAGGCAGCAGTGGGGAATATTGCACAATGG
GCGCAAGCCTGATGCAGCCATGCCGCGTGTATGAAGAAGGCCTTCGG
GTTGTAAAGCACTTTCAGTCGTGAGGAAGGTAGTGTAGTTAATAGCTG
CATTATTTGACGTTAGCTACAGAAGAAGCACCGGCTAACTCCGTGCCA
GCAGCCGCGGTAATACGGAGGGTGCGAGCGTTAATCGGAATTACTGG
GCGTAAAGCGCATGCAGGTGGTTTGTTAAGTCAGATGTGAAAGCCCGG
GGCTCAACCTCGGAATAGCATTTGAAACTGGCAGACTAGAGTACTGTA
GAGGGGGGTAGAATTTCAGGTGTAGCGGTGAAATGCGTAGAGATCTG
AAGGAATACCGGTGGCGAAGGCGGCCCCTGGACAGATACTGACACT
CAGATGCGAAAGCGTGGGGAGCAAACAGGATTAGATACCCTGGTAGT
CCACGCCGTAAACGATGTCTACTTGGAGGTTGTGGCCTTGAGCCGTGG
CTTTCGGAGCTAACGCGTTAAGTAGACCGCCTGGGGAGTACGGTCGCA
AGATTAAAACTCAAATGAATTGACGGGGGCCCGCACAAGCGGTGGAG
CATGTGGTTTAATTCGATGCAACGCGAAGAACCTTACCTACTCTTGAC
ATCCAGAGAACTTTCCAGAGATGGATTGGTGCCTTCGGGAACTCTGAG
ACAGGTGCTGCATGGCTGTCGTCAGCTCGTGTTGTGAAATGTTGGGTT
AAGTCCCGCAACGAGCGCAACCCTTATCCTTGTTTGCCAGCGAGTAAT
GTCGGGAACTCCAGGGAGACTGCCGGTGATAAACCGGAGGAAGGTGG
GGACGACGTCAAGTCATCATGGCCCTTACGAGTAGGGCTACACACGTG
CTACAATGGCGCATACAGAGGGCGGCCAACTTGCGAAAGTGAGCGAA
TCCCAAAAAGTGCGTCGTAGTCCGGATTGGAGTCTGCAACTCGACTCC
ATGAAGTCGGAATCGCTAGTAATCGTGGATCAGAATGCCACGGTGAAT
ACGTTCCCGGGCCTTGTACACACCGCCCGTCACACCATGGGAGTGGGC
TGCAAAAGAAGTAGGTAGTTTAACCTTCGGGGGGACGCTTACCACTTT
GTGGTTCATGACTGGGGTGAAGTCGTAACAAGGTAGCGCTAGGGGAA
CCTGGGGCTGGATCACCT 3'

FIG. 1

Alphabetical references (A-C and E-G) correspond to the alphabetical references (A-C and E-G) under the Column "Sym." of Table 10 in the Detailed Description
FSW = filtered seawater (negative control)
UST = V. alginolyticus DSM15590

SEQUENCE LISTING

<160> NUMBER OF SEQ ID NOS: 1

<210> SEQ ID NO 1
<211> LENGTH: 1490
<212> TYPE: DNA
<213> ORGANISM: Vibrio proteolyticus or Vibrio alginolyticus

<400> SEQUENCE: 1

```
aagtcgagcg gaaacgagtt atctgaacct tcggggaacg ataacggcgt cgagcggcgg      60
acgggtgagt aatgcctagg aaattgccct gatgtggggg ataaccattg gaaacgatgg     120
ctaataccgc atgatgccta cgggccaaag aggggggacct tcgggcctct cgcgtcagga    180
tatgcctagg tgggattagc tagttggtga ggtaagggct caccaaggcg acgatccctta   240 gctggtctga gaggatgatc agccacactg gaactgagac acggtccaga ctcctacggg    300
aggcagcagt ggggaatatt gcacaatggg cgcaagcctg atgcagccat gccgcgtgta    360
tgaagaaggc cttcggggttg taaagcactt tcagtcgtga ggaaggtagt gtagttaata   420
gctgcattat ttgacgttag ctacagaaga agcaccggct aactccgtgc cagcagccgc    480
ggtaatacgg agggtgcgag cgttaatcgg aattactggg cgtaaagcgc atgcaggtgg   540
tttgttaagt cagatgtgaa agcccggggc tcaacctcgg aatagcattt gaaactggca    600
gactagagta ctgtagaggg gggtagaatt tcaggtgtag cggtgaaatg cgtagagatc    660
tgaaggaata ccggtggcga aggcggcccc ctggacagat actgacactc agatgcgaaa    720
gcgtggggag caaacaggat tagataccct ggtagtccac gccgtaaacg atgtctactt    780
ggaggttgtg gccttgagcc gtggctttcg gagctaacgc gttaagtaga ccgcctgggg    840
agtacggtcg caagattaaa actcaaatga attgacgggg gcccgcacaa gcggtggagc    900
atgtggttta attcgatgca acgcgaagaa ccttacctac tcttgacatc cagagaactt    960
tccagagatg gattggtgcc ttcgggaact ctgagacagg tgctgcatgg ctgtcgtcag   1020
ctcgtgttgt gaaatgttgg gttaagtccc gcaacgagcg caacccttat ccttgtttgc    1080
cagcgagtaa tgtcgggaac tccagggaga ctgccggtga taaaccggag gaaggtgggg   1140
acgacgtcaa gtcatcatgg cccttacgag tagggctaca cacgtgctac aatggcgcat   1200
acagagggcg gccaacttgc gaaagtgagc gaatcccaaa aagtgcgtcg tagtccggat    1260
tggagtctgc aactcgactc catgaagtcg gaatcgctag taatcgtgga tcagaatgcc    1320
acggtgaata cgttcccggg ccttgtacac accgcccgtc acaccatggg agtgggctgc   1380
aaaagaagta ggtagtttaa ccttcggggg gacgcttacc actttgtggt tcatgactgg   1440
ggtgaagtcg taacaaggta gcgctagggg aacctggggc tggatcacct               1490
```

ANTI-FOULING EXOPOLYSACCHARIDES ISOLATED FROM CULTURES OF *VIBRIO ALGINOLYTICUS* AND *VIBRIO PROTEOLYTICUS*

FIELD OF INVENTION

The present invention is related to anti-fouling agents. In particular, the present invention is related to naturally occurring anti-fouling agents and biological agents for the production thereof.

BACKGROUND OF INVENTION

For industries operating in the marine environment biofouling, i.e. the unwanted colonization of man-made structures by bacterial slimes, macroorganisms and macroalgae, has significant economic implications. Submerged surfaces such as water pipes, power plant water intake systems, sewer pipes, boat hulls, propellers, heat exchangers, grids, fish nets and cages, and the like are prone to marine biofouling. Aquatic pests frequently clog pipes or become attached to submerged surfaces and thus interfere with normal operations. For example, warm water associated with power plant cooling systems provides an ideal environment for the attachment and growth of aquatic organisms. Biofouling organisms also attach to other surfaces in the aquatic environment such as fishing nets, buoys, pilings, off-shore platforms, lumber, and concrete. When a clean surface is introduced into an aquatic environment, it typically becomes coated with a conditioning layer of hydrophobic dissolved organic compounds (Rittschof D. 1997 In Fingerman M et. al. (eds) *Recent advances in marine biotechnology*, Vol. 3. Science Publishers, Inc., NH, pp. 245–257). Microorganisms such as bacteria, algae, fungi, and protozoa attach to the conditioning layer and establish colonies, which result in the formation of a slime layer (Clare et al., 1992 *Invert Reprod Dev* 22:67–76). Such slimes contribute to the establishment of biofouling communities because planktonic (free floating) larvae of many invertebrate biofouling organisms are physically and chemically attracted to the slime layer (Wieczorek et al., 1997 *Mar Ecol Prog Ser* 119:221–226). Biofouling organisms with a calcareous shell or tubes are particularly troublesome and include mussels, tubeworms and barnacles. Biofouling of underwater structures results in significant economic losses to industry. Decreased fuel efficiency, increased cleaning and maintenance expenses, as well as outage expenses all contribute to increased economic expenditures (Rittschof D. 1997 In Fingerman M, Nagabhushanam R, Thompson M-F (eds) *Recent advances in marine biotechnology*, Vol. 3. Science Publishers, Inc., NH, pp. 245–257).

The incentive for preventing marine biofouling is great. As a result, various methods and compositions have been developed for the prevention of marine biofouling. For example, utilities employ several methods for removing established biofouling communities. Periodic power outages are employed to physically enter power plant systems to remove organisms and debris. In addition, utilities often attempt to kill established biofouling communities by pumping large volumes of chlorine or other biocides through water handling systems. However, these methods are slow acting and adversely affect the local ecology downstream from the effluent. Furthermore, these chemical treatments are inefficient because toxins are mixed in bulk water phase in an attempt to treat a surface phenomenon. Another drawback of certain existing chemical treatments is that relatively large toxic doses must be maintained for extended periods to effectively eliminate biofouling pests (Rittschof D. 1997 In Fingerman M, Nagabhushanam R, Thompson M-F (eds) *Recent advances in marine biotechnology*, Vol. 3. Science Publishers, Inc., NH, pp. 245–257). Ablative toxic antifouling coatings containing tributyl tin, copper alloys, mercury compounds, or cathodic protection have also been employed to control fouling. These antifouling coatings include toxins, which are leached into the aquatic environment to inhibit biofouling (Rittschof D. 1997 In Fingerman M, Nagabhushanam R, Thompson M-F (eds) *Recent advances in marine biotechnology*, Vol. 3. Science Publishers, Inc., NH, pp. 245–257). The most widely used chemical antifoulant compound is tri-n-butyl tin (TBT). High concentrations of TBT have been found in sediments particularly in harbors and along commercial shipping routes (Hashimoto et al., 1998 *Mar Environ Res* 45: 169–177). The adverse effects of TBT and its' derivatives on the marine environment have been recognized for some time, particularly their androgenic effect (Fisher et al. 1999 *Mar Environ Res* 47: 185–201; Mathiessen P., Gibbs P. E. 1998 *Environ Toxicol Chem* 17: 37–43). In response to these concerns Marine Environment Protection Committee (MEPC) of the International Maritime Organization (IMO) has developed an instrument to ban the application of tributyltin paints from 1 Jan. 2003, with the intent that no TBT paints will remain on vessels after 1 Jan. 2008 (http://www.imo.org/conventions).

Vessels are increasingly painted with copper-based paints as an alternative to TBT paints. However, these "alternatives" have negative effects on the marine environment, too, e.g. oysters accumulate considerable amounts of copper and it is toxic to marine algae (Claisse & Alzieu 1993 *Mar Pollut Bull* 26: 395–397). Concerns about the toxicity of not only TBT, but also all antifouling biocides has stimulated research and development of non-toxic, fouling release coatings. Therefore, the development of a marine paint or paint ingredient that is non-toxic, non-heavy-metal-based and benign to the marine environment is urgently sought. A preemptive antifouling composition is needed for treating surfaces in aquatic environment in a highly effective manner.

It is therefore an object of the present invention to provide a method of producing an anti-fouling agent and a composition derived therefrom.

SUMMARY OF INVENTION

In accordance with the present invention, there is provided in one aspect an anti-fouling agent derived by culturing *Vibrio alginolyticus* or *Vibrio proteolyticus* in an aqueous solution suitable for growth thereof. The anti-fouling agent is produced and secreted by these two *Vibrio* species, and can then be used as a component to produce other anti-fouling compositions. Depending on the use, the anti-fouling agent derived from *V. alginolyticus* or *V. proteolyticus* may be used directly, or subject to further purification.

In the preferred embodiment, the anti-fouling agent that is produced and secreted into the fermentation medium by the above-identified *Vibrio* species may be further purified by separating the bacterial cells from the culture medium, and then desalting the cell-free medium. In another preferred embodiment, the anti-fouling agent may be concentrated by any conventional techniques, and used directly or incorporated into appropriate compositions such as, but not limited to paint, concrete, coating for rendering the anti-fouling effect thereto.

In another aspect of the present invention, a method for producing an anti-fouling agent is provided. In its simplest form, the method involves culturing *Vibrio alginolyticus* or *Vibrio proteolyticus* in a suitable medium such that the anti-fouling agent is secreted therein. For certain purposes, such a crude method is adequate to produce sufficient quantity and concentration of the agent for use. In the preferred method, the cells are further separated from the culturing medium, and/or the agent may be further purified and concentrated using conventional means.

In a further aspect of the present invention, the method of producing the anti-fouling agent may be done by culturing various *Vibrio* species, and first testing them to identify species or strains that produce one or more anti-fouling agent(s) using conventional bioassays for the desired fouler. Thereafter, the selected anti-fouling agent(s) may be produced using the same method described above by further culturing the identified *Vibrio* species or strain. The testing methods to identify the useful strains are described in the following detailed description. Clearly, the *Vibrio* species or strain identified according to this method may be acquired from a biological depository or isolated from the environment.

In another aspect, the present invention provides a method of reducing fouling on marine surfaces, which includes the step of applying an anti-fouling agent produced from *Vibrio alginolyticus* or *Vibrio proteolyticus* onto the surface. The application of the agent may be, by way of example only, in the form of a permanent coating or at least one spray or rinsing fluid.

There are clear advantages for using the present invention for anti-fouling purposes. The agent produced from *Vibrio alginolyticus* or *Vibrio proteolyticus* does not contain heavy metals or synthetic toxins that adversely affect the local ecology. The agent can be easily produced with the well-developed methods for cultivation of bacteria and commercially available fermenting equipment. More importantly, this agent inhibits larval settlement of marine macrofoulers in a non-toxic fashion.

In a further aspect, a newly isolated strain of *Vibrio alginolyticus* with strain designation DSM 15590 is provided having characteristics described in detail in the following section.

BRIEF DESCRIPTION OF FIGURES

FIG. 1 shows the DNA sequence coding for the 16S rRNA (SEQ. ID NO:1) of the newly isolated strain DSM 15590.

DETAILED DESCRIPTION

Figure 2:
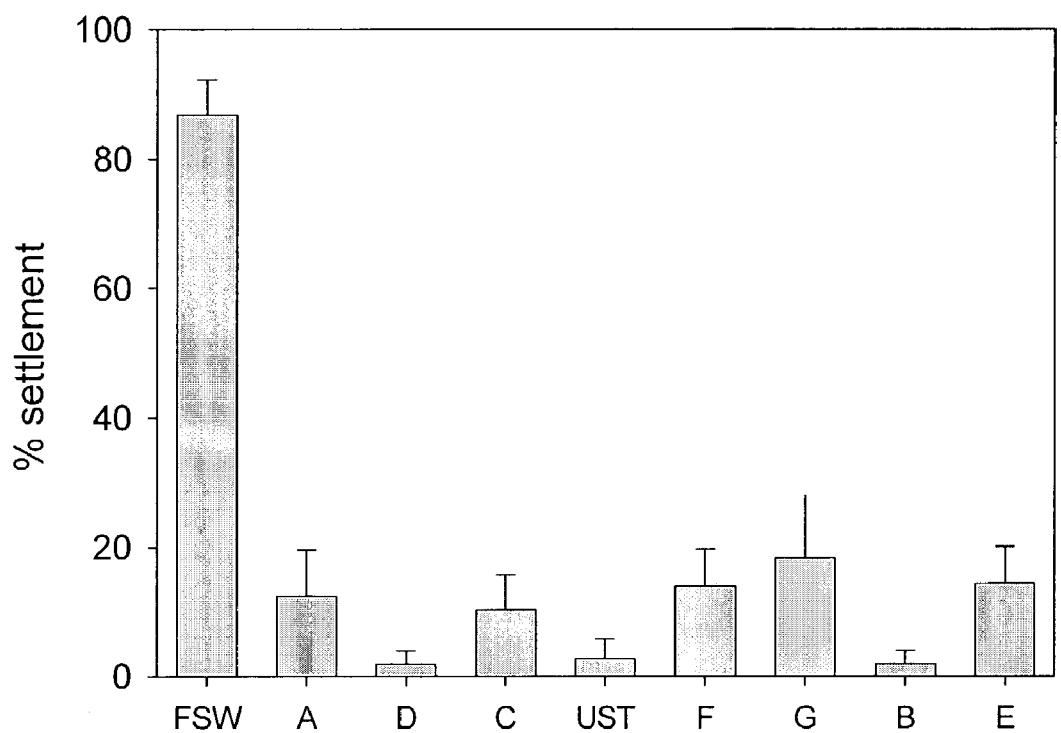
FIG. 2 shows the results of the comparative studies of the antifouling activity of different *Vibrio alginolyticus* and *Vibrio proteolyticus* strains.

The present invention is based on the discovery that a *Vibrio alginolyticus* strain of bacteria secretes a high molecular weight compound that has inhibitory activity on larval attachment and metamorphosis of bryozoan, barnacle and polychaete. This newly isolated strain of *Vibrio alginolyticus* was purified and characterized by the inventors. It is an epibiotic bacterium isolated from the marine macroalga *Ulva reticulata* (*Forsskal*) (*Chlorophyta, Ulvaceae*). This is a marine green macroalga widely abundant on hard substrates in the eastern coastal waters of Hong Kong. The newly isolated strain of *Vibrio alginolyticus* bacterium has been deposited at the "Deutsche Sammlung von Mikroorganismen und Zellkulturen GmbH" (Braunschweig, Germany) under the accession number DSM 15590 on 30 Apr. 2003. This newly isolated strain may also be referred to as the UST strain.

A purified antifouling agent of the present invention was derived from strain DSM 15590.

The bacterium has been purified by enrichment techniques and was identified as *Vibrio alginolyticus* based on comparative analysis of the 16S rRNA DNA sequence and specific substrate utilization. In suspension culture this bacterium exudes compounds of high-molecular weight that can be harvested by ultrafiltration. This high-molecular weight fraction exhibits prominent activity against larval attachment and metamorphosis of a broad array of marine invertebrates, i.e. the polychaete *Hydroides elegans*, the barnacle *Balanus amphitrite* and the bryozoan *Bugula neritina*, all of which have been recognized as fouling organisms on global scale. In contrast to the majority of currently employed biocides, the antifouling effect of the agent according to the present invention is not only non-toxic but its action is also reversible, i.e. after exposure to the agent the instinctive larval settlement process continues normally on unaffected marine surfaces.

The biologically active component in the bacterial exudates has been purified by bioassay-guided gel-chromatography and was correlated with a single band on a denaturing polyacrylamide gel. Specific staining reactions identified the antifouling agent as a polysaccharide of about 200 kD. The monomer composition of the polysaccharide has been identified by glycosyl composition analysis. Once released into the marine environment, polysaccharides are readily susceptible to microbial degradation and thus do not bio-accumulate. Therefore, the possible detrimental effect of this compound on the marine environment will be minimal once it is encapsulated in antifouling coatings on industrial scale.

In contrast to other natural products with antifouling properties derived from marine macroorganisms (e.g. U.S. Pat. Nos. 4,788,302, 5,607,741, 5,695,552, 5,989,323), which require the aquaculture of macro-organisms for a large-scale production of natural antifouling agents, the bacterial products described herein can be generated biotechnologically in large scale utilizing commercially available fermenting technology. This advantage highlights the potential commercialization of the bacteria-derived antifouling agent. Utilizing the identified bacterium, the production of antifouling agents does not rely on aquaculture technology, which is restricted to coastal manufacturers, is labor intensive and further restricted by climatic conditions. The commercial production of the bacteria-derived antifouling agent, however, bears no geographical restrictions since it can easily be performed in land-based fermenters.

The inventors have also tested other publicly available strains of *Vibrio alginolyticus*, and have found that each of these can also produce at least one compound with similar activity, the details of which are also described below. In the course of their testing, one publicly available strain, ATCC 19108, which was classified as a *Vibrio alginolyticus* strain, did not show the characteristic appearance of *Vibrio alginolyticus* during culture, and further sequencing of its 16S RNA DNA revealed that it should be more appropriately classified as being a strain of *Vibrio proteolyticus*. From the information provided below, and from the testing method provided therein, other species of *Vibrio*, such as *V. proteolyticus, V. carchariae, V. harveyi, V. campbellii,* and *V.*

*parahaemolyticus* may also be tested accordingly, and any anti-fouling agent(s) produced therefrom.

The following is a detailed description of the production, characterization and use of the antifouling agent(s) of the present invention.

1. Characterization of One of the Antifouling Agent-producing Bacterium

The bacterial strain according to one aspect of the present invention has been deposited at "Deutsche Sammlung von Mikroorganismen und Zellkulturen GmbH" under the accession number DSM 15590. This bacterium was identified as *Vibrio alginolyticus* by comparative analysis of 16S rRNA DNA sequences as shown in FIG. 1, and phenotypically by growth characteristics on TCBS (Thiosulfate-Citrate-Bile-Sucrose) agar and the pattern of carbon source metabolism. The fatty acids and the said bacterium are given below as additional identifying characteristics.

1.1 Growth Conditions

Under aerobic conditions, suspension cultures of *V. alginolyticus* reach the stationary phase of growth within 24 hrs under vigorous mixing and aeration. Growth conditions at different combinations of temperature and salinity are shown in Table 1 below. The growth was measured by turbidimetry at 610 nm. Measurements were based on 5 replicates. Optimal growth conditions of *V. alginolyticus* (DSM 15590) were achieved in a nutrient medium prepared from 0.5% (w/v) peptone and 0.3% (w/v) yeast extract in 0.22 μm-filtered seawater of 25–45 ppt (parts per thousands) at 20–30° C.

TABLE 1

| Temperature | Abs (610 nm) ± SD | | | | |
|---|---|---|---|---|---|
| (° C.) | 45 ppt | 35 ppt | 25 ppt | 15 ppt | 5 ppt |
| 15 | 0.95 ± 0.03 | 1.06 ± 0.11 | 0.89 ± 0.02 | 0.89 ± 0.04 | 0.04 ± 0.01 |
| 20 | 1.07 ± 0.08 | 1.16 ± 0.09 | 1.34 ± 0.09 | 1.27 ± 0.06 | 0.94 ± 0.04 |
| 30 | 1.48 ± 0.08 | 1.05 ± 0.08 | 1.15 ± 0.04 | 0.84 ± 0.06 | 0.70 ± 0.05 |
| 37 | 0.95 ± 0.03 | 1.08 ± 0.05 | 1.14 ± 0.06 | 1.05 ± 0.08 | 0.71 ± 0.06 |

1.2 Growth Form on TCBS (Thiosulfate-Citrate-Bile-Sucrose) Agar:

small, yellow colonies 1.1 Utilization of carbon substrates as determined by BIOLOG MICROLOG2-system (Biolog, mc; USA) as described in the users' manual.

Table 2 summarizes the carbon utilization characteristics of DSM 15590 and ATCC 17749 (ATCC 17749 being the type strain of *V. alginolyticus*), which was determined by using BIOLOG MICROLOG2-system (microbial identification system).

TABLE 2

| Substrate | DSM 15590 | ATCC 17749 | Substrate | 15590 | ATCC 17749 |
|---|---|---|---|---|---|
| α-Cyclodextrin | + | + | α-Ketobutyric acid | − | − |
| Dextrin | + | + | α-Ketoglutaric acid | + | W |
| Glycogen | + | + | α-Ketovaleric acid | − | − |
| Tween 40 | + | W | D, L-lactic acid | + | + |
| Tween 80 | + | + | Malonic acid | − | − |
| N-acetyl-D-galactosamine | − | − | Propionic acid | + | + |
| N-acetyl-D-glucosamine | + | + | Quinic acid | − | − |
| Adonitol | − | − | D-saccharic acid | − | − |
| L-arabinose | − | − | Sebacic acid | − | − |
| D-arabitol | − | − | Succinic acid | + | + |
| D-cellobiose | W | + | Bromosuccinic acid | + | + |
| L-erythritol | − | − | Succinic Acid | − | − |
| D-fructose | + | + | Glucuronamide | − | − |
| L-fucose | − | − | L-alaninamide | + | + |
| D-galactose | + | − | D-alanine | + | + |
| Gentiobiose | − | − | L-alanine | + | + |
| α-D-glucose | + | + | L-alanyl-glycine | + | + |
| m-inositol | − | − | L-asparagine | + | + |
| α-D-lactose | − | − | L-aspartic acid | + | + |
| Lactulose | − | − | L-glutamic acid | + | + |
| Maltose | + | + | Glycyl-L-aspartic acid | + | + |
| D-mannitol | + | + | Glycyl-L-glutamic acid | + | + |

TABLE 2-continued

| Substrate | DSM 15590 | ATCC 17749 | Substrate | 15590 | ATCC 17749 |
|---|---|---|---|---|---|
| D-mannose | + | – | L-histidine | + | + |
| D-melibiose | – | – | Hydroxy-L-proline | + | W |
| β-methyl-D-glucoside | – | – | L-leucine | – | – |
| D-palcose | W | W | L-ornithine | – | – |
| D-raffinose | – | – | L-phenylalanine | – | – |
| L-rhamnose | – | – | L-proline | + | W |
| D-sorbitol | – | – | L-pyroglutamic acid | – | – |
| Sucrose | + | + | D-serine | – | – |
| D-trehalose | + | + | L-serine | + | + |
| Turanose | – | – | L-threonine | + | + |
| Xylitol | – | – | D, L-carnine | – | – |
| Pyruvic acid methyl ester | + | – | γ-aminobutyric acid | – | – |
| Succinic acid monomethyl ester | W | + | Urocanic acid | – | – |
| Acalic acid | + | + | Inosine | + | + |
| Cis-aconitic acid | + | – | Uridine | + | + |
| Citric acid | – | – | Thymidine | + | + |
| Formic acid | – | + | Phenylethyl-amine | – | – |
| D-galactonic acid lactone | – | – | Putrescine | – | – |
| D-galacturonic acid | – | – | 2-Aminoethanol | + | W |
| D-gluconic acid | + | + | 2,3-Butanodiol | – | – |
| D-glucosaminic acid | – | – | Glycerol | + | + |
| D-glucuronic acid | – | – | D, L-α-glycerol phosphate | – | + |
| α-hydroxybutyric acid | W | + | α-D-glucoso-1-phosphate | + | + |
| β-hydroxybutyric acid | – | – | D-glucose-5-phospate | + | + |
| γ-hydroxybutyric acid | – | – | Laconic acid | – | – |
| p-hydroxy-phenlyacetic acid | – | – | | | |

+, positive;
–, negative;
W, weakly positive

1.4 Fatty Acid Profile of DSM 15590

Fatty acid profiles in bacterial colonies DSM 15590 and ATCC 17749 grown on nutrient agar (0.5% (w/v) peptone, 0.3% (w/v) yeast extract, 1.5% agar in 0.22 μm-filtered seawater) were analyzed by using the MIDI Sherlock Microbial Identification System (MIDI, Inc; USA) as described in the users' manual. Results are shown in Table 3.

TABLE 3

| Fatty acid | DSM 15590 % | ATCC 17749 (Type strain) % |
|---|---|---|
| 7-hydroxy-decanoic acid | 0.15 | Not present |
| Dodecanoic acid | 3.28 | 3.01 |
| 8-hydroxy-undecanoic acid | 0.51 | 0.68 |
| Unknown | 0.48 | 0.67 |
| 12-methyl-dodecanoic acid | 0.72 | Not present |
| Tridecanoic acid | 0.25 | Not present |
| 9-hydroxy-dodecanoic acid | 2.96 | 3.41 |
| Tetradecanoic acid | 4.56 | 4.65 |
| 14-methyl-tetradecenoic acid, 10-hydroxy-tridecanoic acid | 0.62 | 0.89 |
| Pentadecanoic acid | 0.27 | 3.05 |
| Cis-7-pentadecenoic acid | 0.34 | Not present |
| Cis-9-pentadecenoic acid | 0.27 | Not present |
| Pentadecanoic acid | 2.71 | Not present |
| 10-hydroxy-13-methyl-tridecanoic acid | 0.25 | Not present |
| 15-methyl-pentadecenoic acid, 11-hydroxy-tetradecanoic acid | 3.79 | 3.70 |
| 15-methyl-pentadecanoic acid | 1.44 | 2.26 |
| 12-hydroxy-14-methyl-tetradecanoic acid, cis-9-hexadecenoic | 35.04 | 39.59 |
| Hexadecanoic acid | 14.75 | 11.97 |
| 11-hydroxy-14-methyl-tetradecanoic acid | 0.32 | Not present |

TABLE 3-continued

| Fatty acid | DSM 15590 % | ATCC 17749 (Type strain) % |
|---|---|---|
| 16-methyl-hexadecanoic acid | 0.77 | Not present |
| Cis-9-heptadecenoic acid | 3.09 | 3.57 |
| Cis-11-heptadecenoic acid | 0.96 | 1.26 |
| Heptadecanoic acid | 2.49 | 2.47 |
| Cis-11-octadecenoic acid | 18.86 | 18.83 |
| Octadecanoic acid | 0.81 | Not present |
| 11-methyl-cis-11-octadecenoic acid | 0.33 | Not present |

1.5 Partial Purification of the Antifouling Agent Produced by DSM 15590

1.5.1 Batch Fermentation in Suspension

To yield crude samples with antifouling activity of DSM 15590 by fermenting technology, stationary phase cultures of the bacterial strain are centrifuged at 5000×g or filtered through 0.22 μm. The bacterial pellet or the filter residue are washed and subsequently resuspended in seawater. The bacterial suspension is incubated at 25–30° C. for 24 hrs after which the cells are again pelleted or filtered. The cell free supernatant contains the antifouling agent. The bioactive crude sample is desalted by ultrafiltration via membranes with a cut-off value of 100 kilodalton. The same procedure can be utilized to concentrate the antifouling agent. This procedure yields 0.035 g (freeze dry weight) partially purified antifouling product based on an initial bacterial suspension of 0.25 g (wet weight) bacterial pellet per liter seawater.

1.5.2 Growth in Biofilm Reactor

As an alternative to the methodology above, biofilm reactors can be utilized to generate bioactive crude samples. For this purpose panels filmed with the bacterial strain are submerged in seawater for a period of 3 hours after which the seawater is conditioned with the antifouling compound. The same workup procedures for desalting and concentration apply as stated above.

1.6 Further Purification of the Partially Purified Antifouling Product by Chromatography The partially purified antifouling product was subject to bioassay-guided fractionation by size-exclusion chromatography (SEC) on SEPHACRYL-400 (gel filtration media for the separation of macromolecules) (1.6×30 cm) with isochratic elution of 0.1 M phosphate buffer (pH 7) at 0.4 ml/min and monochromatic detection at 220 and 254 nm. Results are shown in FIG. 3 in which the absorbance at 220 nm and 234 nm of each fraction is indicated.

Figure 3:
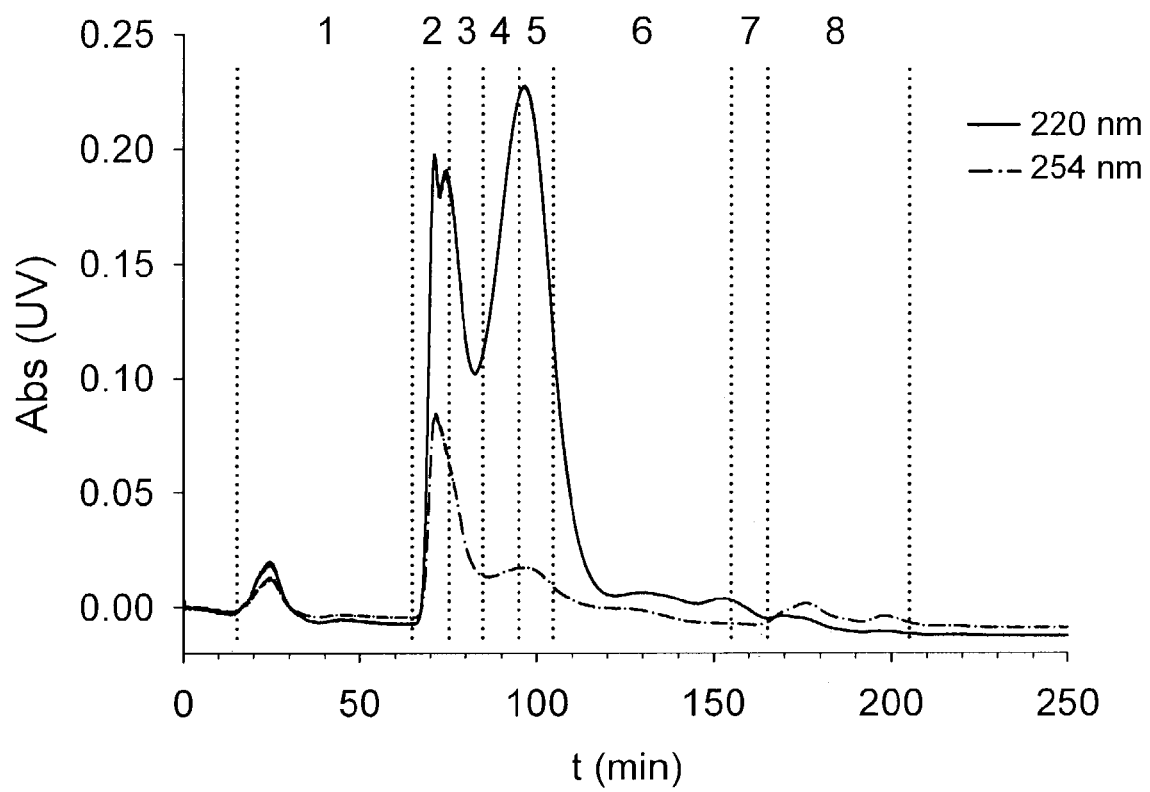
FIG. 3 shows the partial purification results of the antifouling agent of the present invention by chromatographic separation using SEPHACRYL-400 (gel filtration media for the separation of macromolecules).

The vertical dotted lines in FIG. 3 indicate the 8 fractions that were investigated in a larval settlement bioassay of 1 hr with the polychaete *Hydroides elegans*. Briefly, the still water laboratory bioassay was performed with replication (n=5) in sterile polystyrene dishes containing 20 larvae of *H. elegans*, the sample under investigation and an artificial stimulant of larval attachment (3-isobutyl-1-methylxanthine) at $10^{-4}$ M in FSW. After 1 h, dishes were emptied and attached juveniles were counted under the microscope. The results of this assay are summarized in Table 4.

FSW=negative control of filtered seawater.

TABLE 4

|  | FSW | 1 | 2 | 3 | 4 | 5 | 6 | 7 | 8 |
|---|---|---|---|---|---|---|---|---|---|
| Attachment | 73 | 62 | 3* | 11* | 32* | 42* | 70 | 60 | 82 |
| % ± SD | (7.6) | (10.4) | (2.7) | (6.5) | (11.5) | (5.7) | (7.9) | (6.1) | (9.7) |

Data are means ± SD of 5 replicates. Significant statistical differences (Dunnett's multiple pairwise comparison test) are asterisked.

1.8 Antifouling Activity of Partially Purified Antifouling Product Obtained by Bacterial Fermentation Table 5 summarizes the antifouling activity of the partially purified antifouling product of *V. alginolyticus* DSM 15590 on three different types of common fouling organisms, i.e. *Hydroides elegans* (tubeworm), *Bugula neritina* (Bryozoan), and *Balanus amphitrite* (Barnacle). The sample in these assays has been gained by fermentation (3.37 g wet weight bacterial pellet in 400 ml FSW) for 24 h.

The tubeworm bioassay was performed as described above. The larval attachment bioassay with bryozoan *B. neritina* was done according to Bryan et al. (1997 *Mar Ecol Prog Ser* 146: 81–90) and the bioassay with the barnacle *B. amphitrite* was performed according to Maki et al. (1988 *Mar Biol* 97: 199–206). The above references are incorporated in their entirety.

TABLE 5

|  | Settlement % ± SE | | |
|---|---|---|---|
|  | H. elegans (after 24 hr) | B. neritina (after 1 hr) | B. amphitrite (after 24 hrs) |
| Control | 86.0 ± 5.0 | 64.2 ± 9.9 | 68.3 ± 3.3 |
| CSW | 2.8 ± 1.0 | 11.2 ± 6.0 | 45.8 ± 5.5 |

1.8 Antifouling Activity of Partially Purified Antifouling Product Obtained from Biofilm Reactor Table 6 summarizes the antifouling activity of the said product on three different types of common fouling organisms, i.e. *Hydroides elegans* (tubeworm), *Bugula neritina* (Bryozoan), and *Balanus amphitrite* (Barnacle). The sample in these assays has been gained from biofilm reactors as described above (20 cm$^2$ of bacterial film at 5000 cells mm$^{-2}$ in 5 ml seawater) during an exposure time of 3 hrs. FSW=filtered seawater control, FSW*=filtered seawater control with $10^{-4}$ M 3-isobutylmethylxanthine (IBMX, an artificial stimulator of larval settlement in *H. elegans*). Bioassays with *B. neritina* and *B. amphitrite* were run in the absence of IBMX.

TABLE 6

|  | Settlement % ± SE | | |
|---|---|---|---|
|  | H. elegans (after 1 hr) | B. neritina (after 1 hr) | B. amphitrite (after 24 hrs) |
| FSW | 3.0 ± 2.7 | 71.6 ± 15.6 | 66.4 ± 5.3 |
| FSW* | 74.0 ± 15.6 | na | na |
| CSW | 8.0 ± 5.7 | 6.5 ± 5.9 | 42.7 ± 6.9 | na = not applicable 1.9 Gel-electrophoretic Properties and Analytical Results

Figure 4:
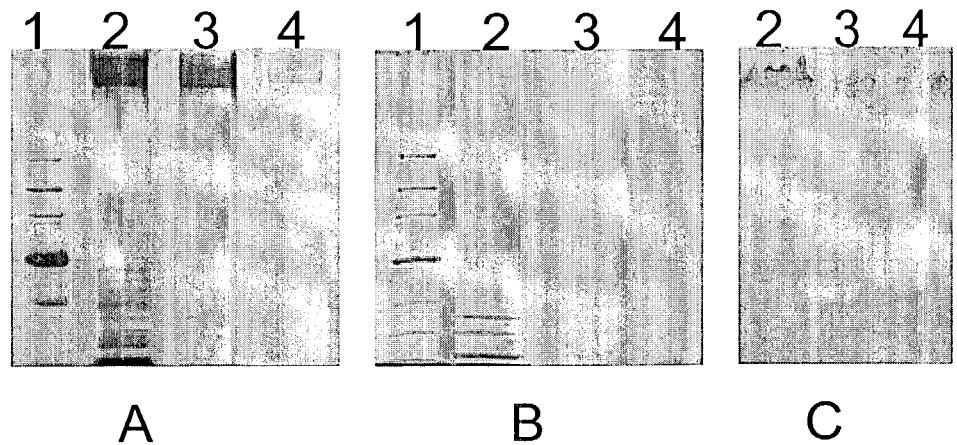
FIG. 4 shows the staining pattern of the antifouling agent of the present invention after electrophoretic separation.

The partially purified antifouling product of *V. alginolyticus* DSM 15590 and the highly bioactive fractions 2 & 3 were subject to SDS-PAGE on 1 mm thick gels of 7.5% polyacrylamide as shown in FIG. 4. After development (200 V, 45 min), gels shown in FIG. 4 were stained with silver (panel A), Coomassie blue R-250 (panel B) and toluidine blue (panel C). Track 1: protein marker (ca. 0.5 mg/ml); Track 2: concentrated partially purified antifouling product (ca. 2 mg/ml carbohydrate); Track 3: SEC-fraction 2; Track 4: SEC-fraction 3. Dominant marker bands are asterisked: d=200 kDa, c=97.2 kDa, b=66.4 kDa, a=26.6 kDa. Electrophoretic characteristics of the antifouling product as shown in FIG. 4 are (1) intensive band with silver stain at the gel entrance in the size range >200 kD; (2) absence of intensive band with Coomassie blue at the gel entrance; and (3) intensive band with toluidine blue at the gel entrance in the size range >200 kD. The absence of Coomassie staining in combination with intensive silver and toluidine blue staining verified the antifouling compound as a polysaccharide.

The results of the glycosyl composition analysis are given in Table 7 and explained below. Glycosyl composition analysis was performed by combined gas chromatography/mass spectrometry (GC/MS) of alditol acetate (AA) derivatives. The sample was hydrolyzed in a sealed tube for 2 h at 121° C. in 2M trifluoroacetic acid (TFA), followed by reduction with sodiumborohydride and acetylation with acetic anhydride/TFA. GC/MS analysis of the alditol acetates was performed on a Hewlett Packard 5890 GC interfaced to a 5970 MSD (mass selective detector, electron impact ionization mode) using a 30 m SUPELCO 2330 bonded phase flused silica capillary column.

TABLE 7

| Glycosyl residue | Mol % |
|---|---|
| Galactose | 11.75 |
| Glucose | 24.22 |
| Heptose | 27.83 |
| N-acetyl glucosamine | 29.33 |
| N-acetyl-galactosamine | 6.86 |

1.10 Ecotoxicity of the antifouling agent secreted by DSM 15590

Ecotoxicity assays of the purified antifouling product of DSM 15590 were performed with larvae of *Bugula neritina*. Briefly, 10 larvae were added to a polystyrene petri dish containing 50 μl of sample under investigation. Each bioassay was performed with replications (n=5) with FSW and solutions of $CuCl_2$ as negative and positive controls correspondingly. After 24h the number of live and dead larvae were counted under the microscope.

TABLE 8

| Treatment | mg/ml | Mortality |
|---|---|---|
| Filtered seawater | — | 0 |
| Copper chloride | 10 | 100 |
| | 1 | 74 ± 6.8 |
| | 0.1 | 6 ± 4 |
| | 0.01 | 0 |
| Purified antifouling product | 10 | 100 |
| | 7.5 | 56 ± 22 |
| | 5 | 0 |

1.11 Reversibility of antifouling effect

After exposure of larvae of *H. elegans* and *B. neritina* to purified antifouling compound at the effective concentration for 24 h, larvae were transferred into new filtered seawater. After additional 24 h, the percentage of settled larvae was determined. The results are summarized in Table 9.

TABLE 9

| | Percentage of swimming larvae | |
|---|---|---|
| Larvae of | In the compound | After the washing |
| H. elegans | 95 ± 2 | 0 |
| B. neritina | 97 ± 1 | 0 |

2. Antifouling agents produced from commercially available *V. alginolyticus*

In this study, different strains of *V. alginolyticus* were tested and compared in antifouling bioassays. The different strains and their origin are listed in Table 10.

TABLE 10

| Strain designation | Sym. | Biological Origin | Remarks |
|---|---|---|---|
| ATCC 14582 | A | Wood suspended in seawater | Subspecies of *V. alginolyticus* |
| ATCC 17749 | B | Spoiled mackerel (*Trachurus trachurus*) causing food poisoning | Type strain of *Vibrio alginolytocus* |
| ATCC 19108 | C | Hard clam (*Mercenaria mercenaria*) | *Vibrio proteolyticus*, formerly known as *V. alginolyticus* |
| CIP 71.3 | D | — | Two stable colony types giving identical gel-electrophoretic protein profiles |
| NCIMB 1318 | E | — | Different from the type strain in phenotypic analysis |
| NCIMB 2047 | F | — | Subspecies of *V. alginolyticus* |
| NCIMB 11038 | G | Cured hides | *V. alginolyticus* chemovar. *Iophagus*. |

Different strains of commercially available *V. alginolyticus* as shown in Table 10 were inoculated into sterile culture broth (0.5% (w/v) peptone, 0.3% (w/v) yeast extract in 0.22 μm-filtered seawater) and grown at 30° C. for 24 h to stationary phase. Suspended bacteria were harvested by centrifugation, washed, and diluted in autoclaved filtered seawater to an optical density of 0.1 at a wavelength of 610 nm. Polystyrene Petri dishes were filled with 4 ml bacterial suspension and incubated for 3 h at 22° C. for the attachment of bacteria after which dishes were dip-rinsed in autoclaved filtered seawater to remove unattached cells. Besides 5 dishes for larval attachment assays, 3 dishes were treated accordingly to enumerate bacteria on the dish surface. The bacterial abundance in experimental films in this experiment ranged between 8000–10,000 cells/mm$^2$. Filmed dishes were filled with 4 ml of filtered seawater and incubated for 1 h at 22° C. to obtain waterborne bacterial products (in the following referred to as conditioned water). Conditioned water was ultra-filtered through 100 kDa membranes and the filter residue was transferred into new dishes. Dishes containing conditioned water samples from different *V. alginolyticus* were subject to larval attachment assays with the bryozoan *Bugula neritina* using the same method as previously described. Larval attachment and metamorphosis were scored after 1 hour and compared with the filtered seawater control (negative control).

As shown in FIG. 2, all the strains under investigation significantly inhibited larval attachment and metamorphosis of the bryozoan Bugula neritina.

While the present invention has been described using the aforementioned figures and the specific examples of DSM 15590 and various publicly available Vibrio alginolyticus species, it is understood that these are examples only and should not be taken as limitation to the present invention. It should also be understood that although the term "antifouling agent" is used in the singular form, it is clear that each Vibrio alginolyticus strain may produce a slightly different agent. However, if a user chooses a pure and single strain for large scale production of the antifouling agent, then it is likely to be a single agent, thus properly described in the singular form. Furthermore, the antifouling agent(s) obtained from the strains as described herein represent some embodiments of the present invention and the same principle of the present invention can also apply to the production of antifouling agents in other strains of the same species using the teaching provided herein.

The invention claimed is:

1. An isolated exopolysaccharide that is over 200 kilodaltons in size as measured by denaturing gel electrophoresis and consists essentially of galacrose, glucose, heptose, N-acetylglucosamine, and N-apetylgalactosamine, said exopolysaccharide being capable of reversibly inhibiting settlement of fouling organisms on underwater surfaces and capable of being produced by a *Vibrio* species selected from the group consisting of *Vibrio alginolytlcus, Vitrio proteolyticus*, and mixtures thereof.

2. The exopolysaccharide according to claim 1, wherein said *Vibrlo* species is *Vibrio alginolyticus* strain DSM 15590.

3. The exopolysaccharide according to claim 1, wherein said exopolysaccharide is produced by a process comprising the steps of:
   culturing a *Vibrio* species selected from the group consisting of *Vibrio alginolyticus, Vibrio proteolyticus*, and mistures thereof in an aqueous solution suitable for growth of said *Vibrio* species until said exopolysaccharide is produced and secreted into said solution;
   separating said *Vibrio* species from said aqueous solution to form a cell-free solution; and
   isolating said exopolysaccharide from said cell-free solution.

4. The exopolysaccharide according to claim 2, wherein said exopolysaccharide is produced by a process comprising: culturing *Vibrio alginolyticus* DSM 15590 in an aqueous solution suitable for growth of said *Vibrio alginolyticus* DSM 15590 until said exopolysaccharide is produced and secreted into said solution;
   separating said Vibrio alginolyticus DSM 15590 from said aqueous solution to form a cell-free solution; and
   isolating said exopolysaccharide from said cell-free solution.

5. An anti-fouling composition comprising the exopolysaccharide of claim 1 and a carrier suitable for use on marine structures.

6. An anti-fouling composition comprising the exopolysaccharide of claim 2 and a carrier suitable for use on marine structures.

7. The composition of claim 5 or claim 6, wherein said carrier is selected from the group consisting of a marine paint, a marine coating, and a mixture thereof.

8. A method of producing the exopolysaccharide of claim 1 comprising the steps of:
   culturing a *Vibrio* species selected from the group consisting of *Vibrio alginolyticus, Vibrio proteolyticus*, and mixtures thereof in an aqueous solution suitable for growth of said *Vibrio* species until said exopolysaccharide is produced and secreted into said solution:
   separating said *Vibrio* species from said aqueous solution to form a cell-free solution; and
   isolating said exopolysaccharide from said cell-free solution.

9. The method of claim 8, wherein said aqueous solution is seawater.

10. The method of claim 9, further comprising the step of desalting said cell-free solution.

11. The method of claim 10, wherein said desalting comprises size separation with a cut-off value of 100 kilodaltons.

12. The method of claim 1, wherein said *Vibrio* species is a strain selected from the group consisting of DMS 15590, ATCC 14582, ATCC 17749, ATCC 19108, CIP 71.3, NCIMB 1318, NCIMB 2047, and NCIMB 11038.

13. A method of reducing fouling on the surface of a marine structure by organisms selected from the group consisting of *Hydroides elegans, Balanus amphitrite*, and *Bugulda neritina* comprising applying the exopolysaccharide of claim 1 to said surface.

14. A method of reducing fouling on the surface of a marine structure by organisms selected from the group consisting of *Hydroides elegans, Balanus amphitrite*, and *Bugula neritina* comprising applying the exopolysaccharide of claim 2 to said surface.

* * * * *

UNITED STATES PATENT AND TRADEMARK OFFICE
CERTIFICATE OF CORRECTION

PATENT NO. : 7,090,856 B2  Page 1 of 1
APPLICATION NO. : 10/465448
DATED : August 15, 2006
INVENTOR(S) : Pei-Yuan Qian et al.

It is certified that error appears in the above-identified patent and that said Letters Patent is hereby corrected as shown below:

Title page abstract: #57 line 4 "anti-fouting" should read --anti-fouling-- line 5 "compositions," should read --compositions.-- line 7 "alginolyricus" should read --alginolyticus-- line 7 "may be use" should read --may be used--

Column 6, line 32: "1.1" should read --1.3--

Column 6, line 33: "mc;" should read --Inc.;--

Column 9, line 40: "1.8" should read --1.7--

Column 15, line 4: "galacrose" should read --galactose--

Column 15, line 5: "N-apetylgalactosamine" should read --N-acetylgalactosamine--

Column 15, line 9: "alginolytlcus" should read --alginolyticus--

Column 15, line 9: "Vitrio" should read --Vibrio--

Column 15, line 12: "Vibrlo" should read --Vibrio--

Column 15, line 19: "mistures" should read --mixtures--

Signed and Sealed this

Twentieth Day of February, 2007

JON W. DUDAS
*Director of the United States Patent and Trademark Office*